United States Patent [19]

VandenBerg

[11] Patent Number: Plant 6,999

[45] Date of Patent: Aug. 22, 1989

[54] CHRYSANTHEMUM PLANT NAME HEKLA

[75] Inventor: Cornelis P. VandenBerg, Salinas, Calif.

[73] Assignee: Yoder Brothers, Inc., Barberton, Ohio

[21] Appl. No.: 247,658

[22] Filed: Sep. 22, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A chrysanthemum plant named Hekla particularly characterized by its flat capitulum form; daisy capitulum type; white ray floret color; diameter across face of capitulum of up to 47 mm at maturity; medium plant height with spreading and prolific branching pattern; average natural season flower date of August 25 in Salinas, Calif. and September 20 in Hightstown, N.J.; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of chrysanthemum, botanically known a *Dendranthema grandiflora,* and referred to by the cultivar name Hekla.

Hekla, identified as 85-094001, was originated from a cross made by the inventor, Cornelis P. VandenBerg, in a controlled breeding program in Salinas, Calif., in 1985.

The female parent and the male parent of Hekla were both unnamed seedlings, identified respectively as 82-M49004 and 83-645001. Hekla was discovered and selected as one flowering plant within the progeny of the stated cross by Cornelis P. VandenBerg in January 1986, in a controlled environment in Salinas, Calif.

The first act of asexual reproduction of Hekla was accomplished when vegetative cuttings were taken from the initial selection in April 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Hekla are firmly fixed and are retained through successive generations of asexual reproduction.

Hekla has not been observed under all possible environmental conditions. The phenotype may vary significantly with variations in environment such as temperature, light intensity and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Hekla, which, in combination, distinguish this chrysanthemum as a new and distinct cultivar:

1. Flat capitulum form.
2. Daisy capitulum type.
3. White ray floret color.

4. Diameter across face of capitulum up to 47 mm at maturity.
5. Medium plant height.
6. Spreading and prolific branching pattern.
7. Average natural season flower date of August 25 in Salinas, Calif., and September 20 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Hekla, with the colors being as nearly true as possible with illustrations of this type. Sheet 1 is a color photograph of Hekla grown as a pinched spray pot mum. Sheet 2 is a black and white photograph of three views of the inflorescence of Hekla. Sheet 3 is a black and white photograph showing the upper and under sides of the leaves of Hekla at three stages of development (mature, intermediate and immature).

Of the commercial cultivars known to the inventor, the most similar in comparison to Hekla is White Stardom, disclosed in U.S. Plant Pat. No. 3,999. Reference is made to attached Chart A, which compares certain characteristics of Hekla to the same characteristics of White Stardom.

Similar traits are ray floret color, branching pattern, plant height and controlled flowering response. Hekla has a true daisy flower form, while White Stardom, with 4 to 5 rows of petals, can be described as a duplex daisy. Hekla has a smaller diameter of capitulum and an earlier natural season flower date than White Stardom. In the following description color references are made to The Royal Horticultural Society Colour Chart. The clear white ray floret color of Hekla is not represented in the R.H.S. Colour Chart. The color values were determined on plant material grown in a controlled greenhouse environment in Salinas, Calif. on May 20, 1988.

CLASSIFICATION

Botanical: *Dendranthema grandiflora.* cv. Hekla.
Commercial: Daisy spray pot mum and garden mum.

INFLORESCENCE

A. Capitulum:
*Form.*—Flat.
*Type.*—Daisy.
*Diameter across face.*—Up to 47 mm at maturity.

B. Corolla of ray florets:
*Color (general tonality from a distance of three meters).*—White.
*Color (upper surface).*—White.
*Color (under surface).*—White.
*Shape.*—Flat, straight, oblong.

C. Corolla of disc florets:
*Color (mature).*—Closest to 13A to 13B.
*Color (immature).*—Closest to 151C, tinged with 144C.

D. Reproductive organs:
*Androecium.*—Present on disc florets only; abundant pollen.
*Gynoecium.*—Present on both ray and disc florets.

PLANT

A. General appearance:
*Height.*—Medium.

*Branching pattern.*—Spreading and prolific.

B. Foliage:
*Color (upper surface).*—137A.
*Color (under surface).*—137B.
*Shape.*—Small, lobed.

CHART A

COMPARISON OF HELKA AND WHITE STARDOM

| | Hekla | White Stardom |
|---|---|---|
| Ray Floret Color | White | White |
| Capitulum Form and Type | Flat Daisy | Flat Duplex Daisy |
| Branching Pattern | Spreading and Prolific | Spreading and Prolific |
| Diameter Across Face of Capitulum | 47 mm | 57 mm |
| Plant Height | Medium | Medium |
| Controlled Response | 7 Weeks | 7 Weeks |
| Average Natural Season Flowerdate | | |
| In Salinas, CA | August 25 | August 29 |
| In Hightstown, NJ | September 20 | September 28 |

COMPARISONS MADE OF PLANTS GROWN UNDER NATURAL SEASON OUTDOOR CONDITIONS IN SALINAS, CALIFORNIA AND HIGHTSTOWN, NEW JERSEY

I claim:

1. A new and distinct chrysanthemum plant named Hekla, as described and illustrated.

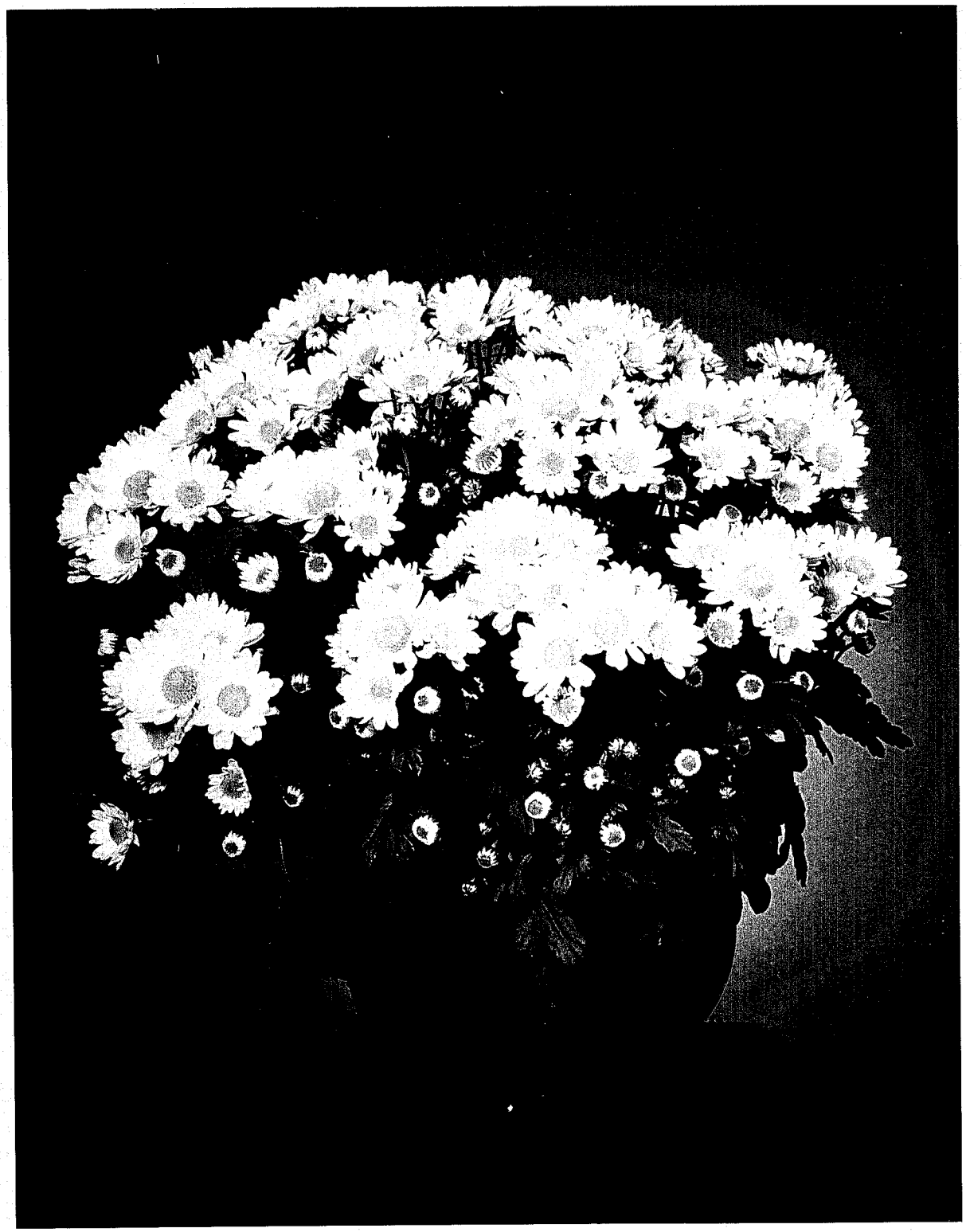

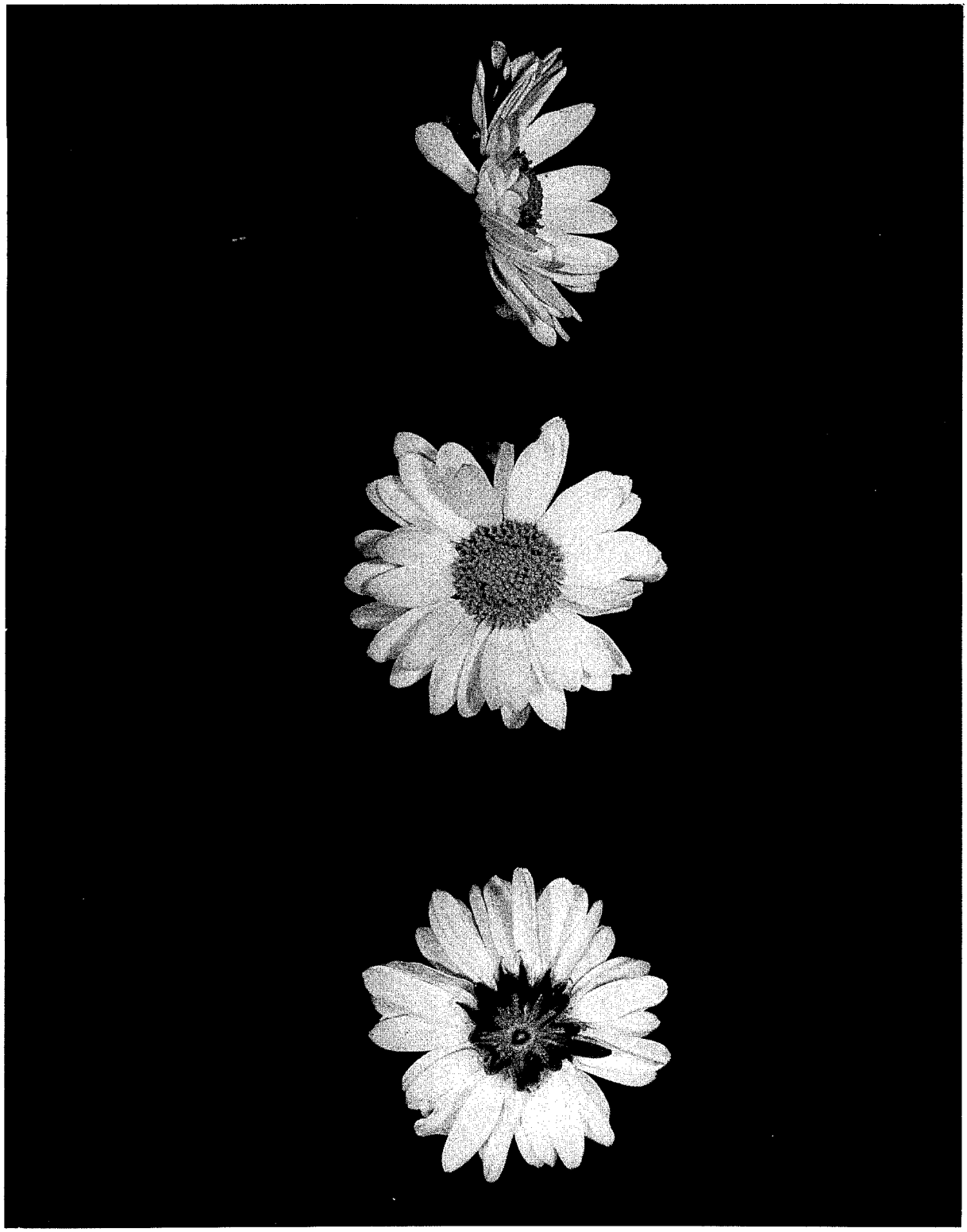

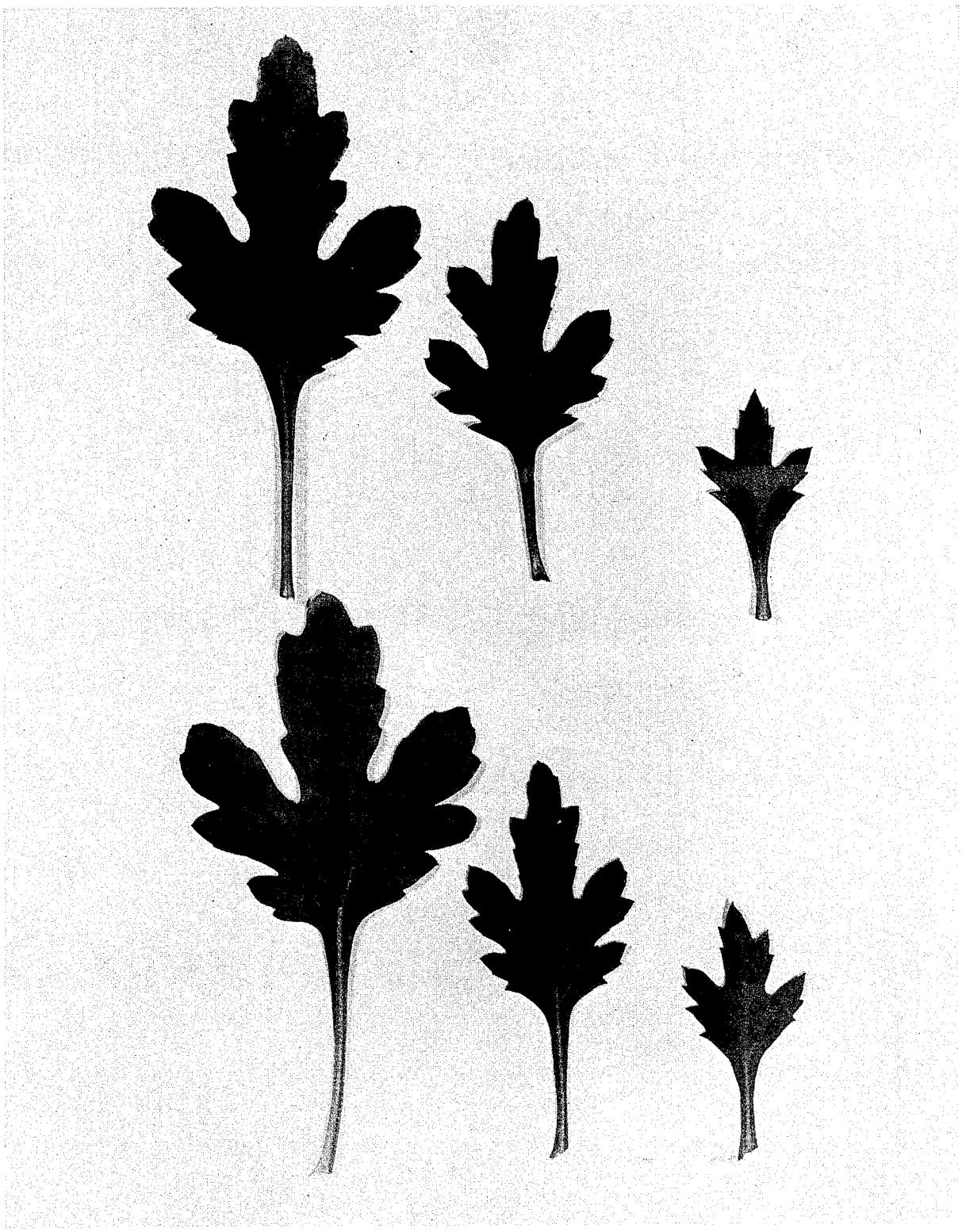

* * * * *